United States Patent [19]
Genese

[11] 3,991,763
[45] Nov. 16, 1976

[54] SURGICAL EVACUATOR

[75] Inventor: Joseph Nicholas Genese, Waukegan, Ill.

[73] Assignee: Arbrook, Inc., Arlington, Tex.

[22] Filed: Apr. 17, 1975

[21] Appl. No.: 569,042

[52] U.S. Cl. ............................................. 128/278
[51] Int. Cl.² ......................................... A61M 1/00
[58] Field of Search ........................... 128/274–278;
137/333, 381, 382; 251/210, 211, 349, 352;
417/472; 27/242

[56] References Cited
UNITED STATES PATENTS

| 972,878 | 10/1910 | Leon | 27/24 R |
|---|---|---|---|
| 3,376,868 | 4/1968 | Mondiadis | 128/278 |
| 3,421,504 | 1/1969 | Gibbons | 128/278 |

Primary Examiner—Robert W. Michell
Assistant Examiner—Henry S. Layton
Attorney, Agent, or Firm—James R. Hulen

[57] ABSTRACT

A wound drainage container for withdrawing and collecting body fluids from a patient is equipped with a valved fluid inlet port and with a fluid outlet port having a one-way valve for emptying the container and for preventing the entry of contaminants into the container. A gate movable between a first position and a second position is provided for actuating the inlet valve. When the gate is in the first position it opens the inlet valve and covers the outlet valve which is located adjacent the inlet valve, and when the gate is in the second position it closes the inlet valve and uncovers the outlet valve so that fluid in the container may be emptied therefrom without the danger of the fluid being flushed back into the patient's wound.

6 Claims, 10 Drawing Figures

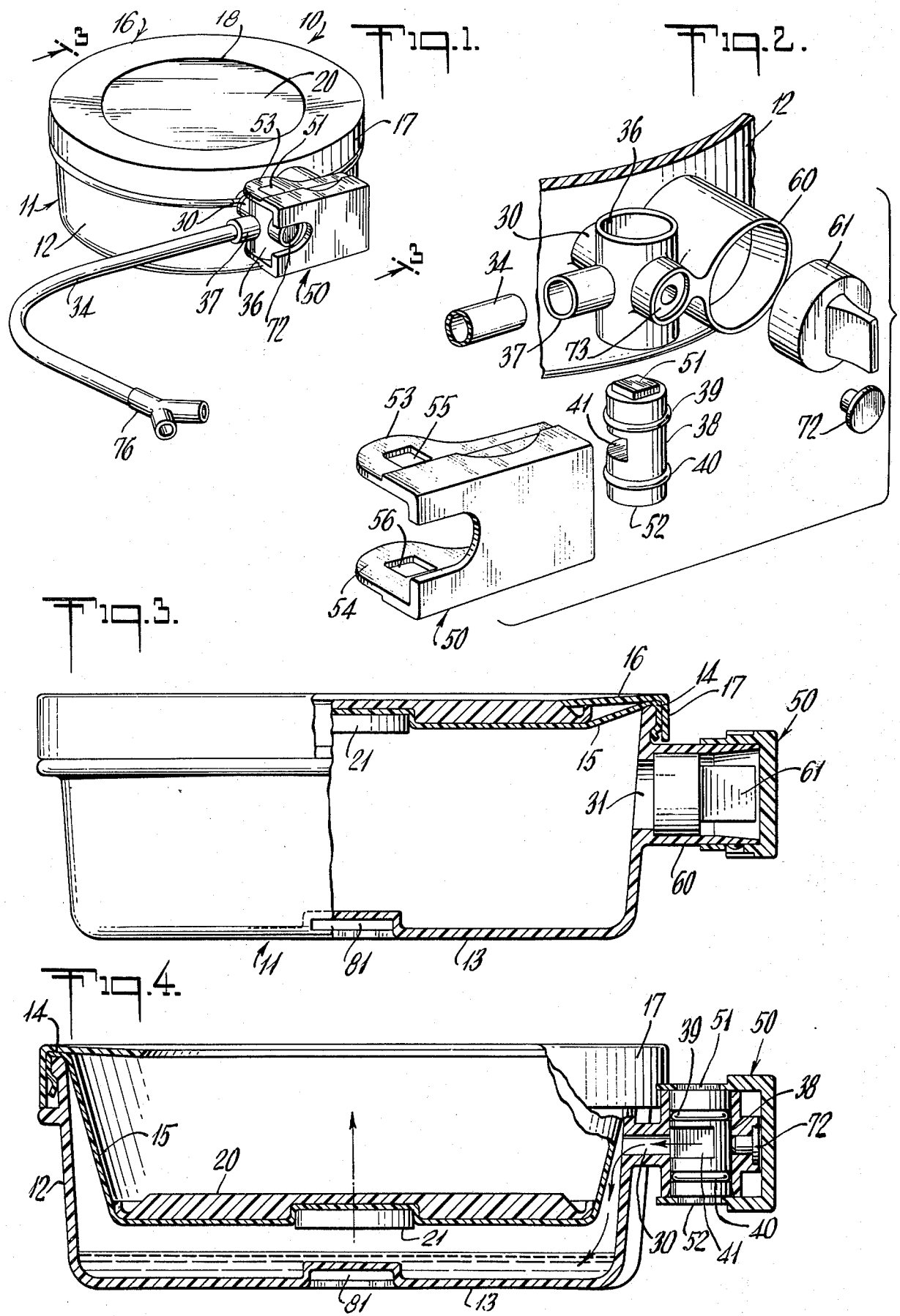

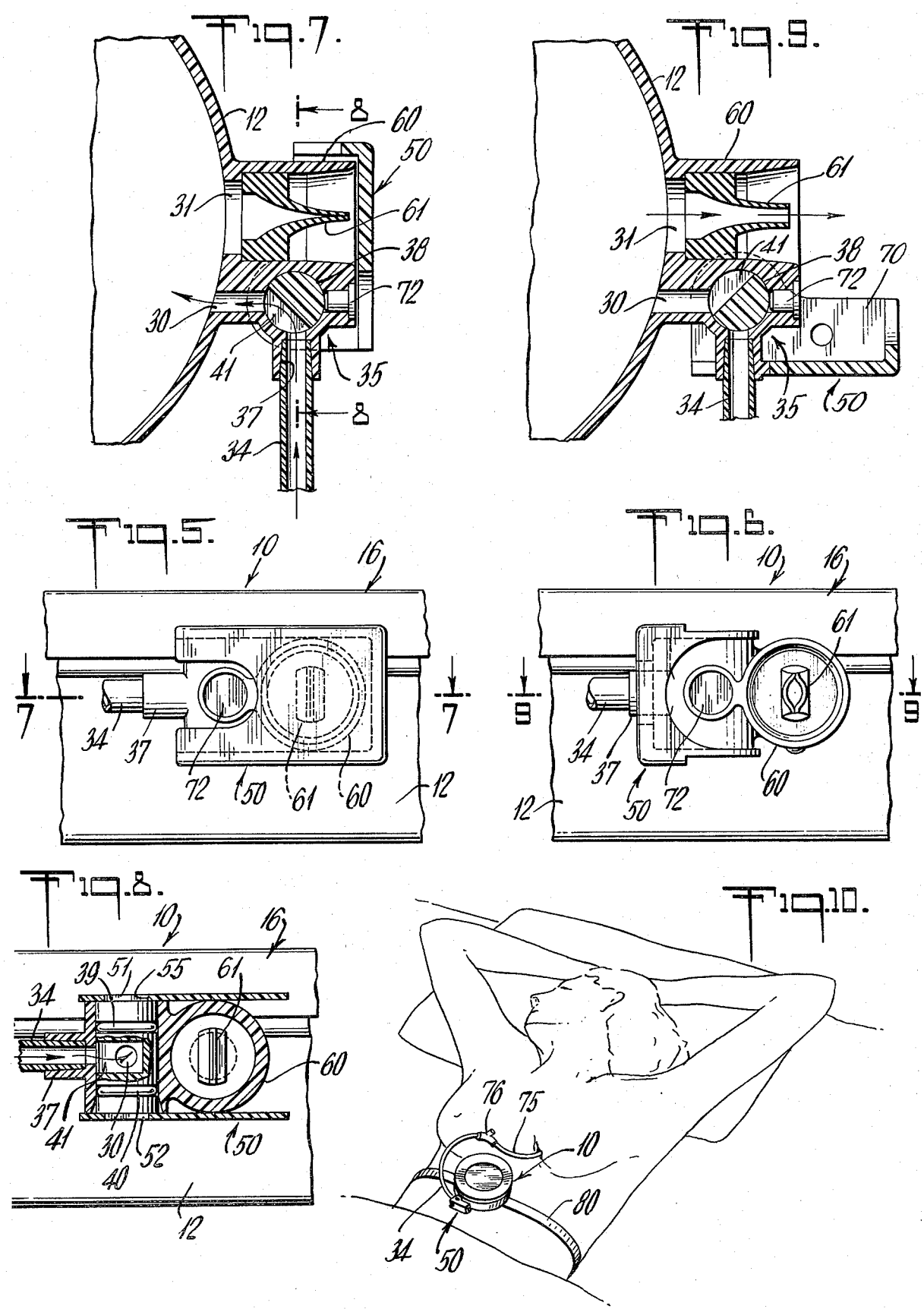

SURGICAL EVACUATOR

BACKGROUND OF THE INVENTION

This invention relates generally to a closed wound suction device and, more particularly, to a unique closed wound suction device having a uniquely designed valve system.

In post-operative surgical procedures, drains are used whenever an abnormal collection of fluid is encountered, be it contaminated or infected material, blood, bile or lymph, exudate or transudate. Ordinary wounds are normally drained for a post-operative period running as long as forty-eight hours. Effective drainage is of medical importance, for swelling and tension are minimized thereby, post-operative pain is reduced, and wound edges are maintained flat and quiescent.

A number of manually-operated wound suction devices are presently in use and, also, a large number of wound suction devices have been described and illustrated in issued United States patents and in other literature. Illustrative of the type of manually-operated wound suction devices within the field of the present invention are those illustrated in U.S. Pat. Nos. 3,115,138 and 3,376,868.

All of the presently known commercial systems have the disadvantage that, whenever it is necessary to empty the fluid collection container, the drainage tubing must be removed from the container and replaced on the container after it has been emptied. This obvious disadvantage creates a serious problem of contamination in that the disconnected tubing is exposed to the environment and contaminants may thereby enter the system and ultimately find their way to the wound site of the patient and, thus, create infection and other post-operative problems.

In order to alleviate this problem, a number of valving systems have been proposed which include one-way valve mechanisms for preventing the back flow of material into the wound site when the containers are actuated to flush material therefrom. Two such devices are illustrated in U.S. Pat. Nos. 3,572,342 and 3,774,611. Both of these systems provide one-way valves in the inlet ports leading from the patient to the container and also additional outlets for the removal of fluid from the containers when it is desired to empty the containers. However, the previously known one-way inlet valves rely on differential pressure between the container and the wound tubing to open the valve to permit the fluid to drain into the container. This is considered to be undesirable in that the inlet valves may be subject to malfunction and, thus, a more positive actuating device for the inlet valve is desirable.

SUMMARY OF THE INVENTION

In view of the foregoing, it is the main object of this invention to provide an exceptionally simple and efficient manually-operated wound suction device which obviates the need for removing the wound drainage tubing from the device for the purpose of emptying the container and, thus, eliminates the contamination problem associated with that manipulative procedure. Also, the present invention provides a unique valving arrangement which permits the container to be emptied by actuating a gate mechanism which closes off the inlet valve and at the same time uncovers the one-way outlet valve. Thereafter, by merely actuating the container, i.e., increasing the internal pressure thereof, the fluid contained therein will be expelled through the one-way outlet valve and the container will be actuated for a subsequent drainage procedure.

To again open the inlet valve it is only necessary to move the actuating gate from the second position to its first position overlying the outlet port.

It will be seen that a unique valve system has been provided that includes closely adjacent inlet and outlet ports in the wall of a fluid collection container, which ports are effected by a single pivotally mounted gate member. Thus, fluid collection and fluid emptying are accomplished in a very simple manner without the danger of contaminants entering the system and infecting the wound site.

BRIEF DESCRIPTION OF THE DRAWINGS

The foregoing objects and many of the attendant advantages of this invention will become more readily appreciated as the same becomes better understood by reference to the following detailed description when taken in conjunction with the accompanying drawings wherein:

FIG. 1 is a perspective view illustrating the unique wound suction device of the present invention.

FIG. 2 is an assembly drawing showing the assembly of the components of the unique valve system of the present invention.

FIG. 3 is a side view of the device of FIG. 1 with parts broken away along line 3—3.

FIG. 4 is a cross sectional view illustrating the diaphragm of the fluid collection container in an actuated downward position.

FIG. 5 is a side view of the valve system with the gate illustrated in the closed position and the underlying valve shown in phantom.

FIG. 6 is a view similar to FIG. 5 but showing the gate in the open position and with the one-way valve shown in an open position.

FIG. 7 is a sectional view taken along line 7—7 in FIG. 5.

FIG. 8 is a sectional view taken along line 8—8 in FIG. 7.

FIG. 9 is a sectional view taken along line 9—9 in FIG. 6.

FIG. 10 is a perspective view illustrating the unique wound suction system of the present invention in combination with the wound of a patient.

DESCRIPTION OF THE PREFERRED EMBODIMENT

Referring to FIG. 1, the closed wound drainage device of the present invention is shown generally at 10. Drainage device 10 comprises a generally rigid bowl 11 having a cylindrical side wall 12 and a bottom wall 13. Bowl 11 is preferably made from a plastic material but may be made of any suitable rigid material. The upper edge 14 of side wall 12 forms an opening over which an elastomeric membrane 15 is secured (see FIGS. 3 and 4). Membrane 15 is securely sealed over edge 14 by an annular cap 16 which has a depending flange 17 around the periphery thereof and a central opening 18. Flange 17 extends downwardly around the outer periphery of edge 14 and securely clamps membrane 15 therebetween.

The material from which membrane 15 is made is not critical so long as the membrane is capable of being stretched to an extent sufficient to displace the atmosphere from bowl 11 as illustrated in FIG. 4. Obviously, the membrane must also have an elastic memory that will permit it to seek its original planar shape after it has been stretched to such a configuration. An actuator disc 20 is secured to the outer surface of membrane 15 by a centrally disposed button 21. Disc 20 is preferably attached centrally to the outer surface of membrane 15 to permit the portion of the membrane lying thereunder to stretch. Both disc 20 and button 21 are preferably made of plastic or other rigid material.

In order to utilize the closed wound drainage device described above, a unique valving system is provided. This valving system will now be described in detail.

Referring first to FIG. 7, the entire valving system is illustrated wherein an inlet port 30 is provided in wall 12 of bowl 11. Also provided adjacent to inlet port 30 is an outlet port 31. As will be seen in FIG. 7, fluid enters bowl 11 through inlet port 30 from a connection tube 34. A rotary valve shown generally at 35 controls the flow of fluid between tube 34 and inlet port 30. Valve 35 is preferably constructed in the form of a rotary valve which can be rotated 90° from an open position as shown in FIG. 7 to a closed position as shown in FIG. 9.

For a better understanding of the construction of valve 35, reference is made to FIG. 2 wherein inlet port 30 is shown extending outwardly through side wall 12 of bowl 11. Inlet port 30 extends into a cylindrical housing 36 that is positioned normal to the inlet. A second cylindrical housing 37 extends into housing 36 at a 90° angle and is adapted to receive connection tube 34. A rotary valve 38 is adapted to slide into housing 36 and a firm seal is formed between housing 36 and valve 38 by a pair of O-rings 39 and 40. A channel 41 is formed in the wall of valve 38 to provide a passageway for fluid from connection tube 34 to inlet 30 when the valve is in the "on" position as illustrated in FIG. 7. In order to place the valve in an "off" position, it is only necessary to rotate the valve 90° to the position illustrated in FIG. 9.

The final assembly of valve 38 within housing 36 is accomplished by positioning a gate 50 over the ends of valve 38 as best illustrated in FIG. 1. The ends of valve 38 are provided with generally square-shaped bosses 51 and 52 and the ears 53 and 54 extending outwardly from gate 50 are provided with mating square apertures 55 and 56 for receiving bosses 51 and 52, respectively.

Referring again to FIG. 7, fluid outlet port 31 is illustrated therein extending through side wall 12 of bowl 11. Port 31 is located directly adjacent port 30 and has a generally cylindrical housing 60 extending outwardly therefrom. A duck-bill valve 61 is securely positioned within cylindrical housing 60 and is adapted to operate as a one-way valve for the explusion of fluids from within bowl 11. Valve 61 is preferably formed in one piece from a relatively soft rubber compound. The design and function of this type of valve is well known in the art.

To complete the structure of the unique valve system of the present invention, gate 50 is provided to perform the dual function of operating rotary valve 38 and for also covering and uncovering outlet port 31. Gate 50, as best illustrated in FIG. 2, has a generally rectangular configuration with an opening 70 (see FIG. 9) that faces housing 60 when the gate is in a position adjacent the housing. A closure 72 is adapted to be placed in opening 73 to form a seal for the opening which is formed within housing 36.

The operation of the unique wound drainage device of the present invention will now be described in detail. Following a surgical procedure in which wound drainage is typically required, a drainage tube 75 (see FIG. 10) is placed into the area to be drained and the wound is closed around the tubing. Drainage tube 75 is then secured to a Y-Connector 76 which is secured to the end of connection tubing 34 which is, in turn, secured to housing 37 extending outwardly from housing 36 in the valve assembly.

If desired, a strap 80 may be secured to bowl 11 by passing the strap through a pair of openings 81 formed in the bottom of the bowl. The strap may then be used to secure bowl 11 to the body of the patient.

In order to actuate the drainage device to form a vacuum therein, gate 50 is placed in the position illustrated in FIG. 9. In this gate position, it is possible to depress disc 20 into bowl 11 to a location as illustrated in FIG. 4. When manual pressure is released from the disc, the disc and attached membrane 15 will remain in the FIG. 4 position and the drainage device will be in an actuated position ready to draw fluids from the wound of the patient. The only step then required is to pivot gate 50 from the position illustrated in FIG. 9 to the position illustrated in FIG. 7. This will not only open valve 38 so that fluid may pass from tubing 34 to inlet port 30 via passageway 41, but the gate will also cover port 31 so that fluid cannot be accidentally expelled from bowl 11 by further depression of disc 20.

When it is desired to empty bowl 11, gate 50 is again pivoted from its first position as illustrated in FIG. 7 to its second position as illustrated in FIG. 9. The operator may then depress disc 20 once again from a position as illustrated in FIG. 3 to the position illustrated in FIG. 4 to thus empty bowl 11 through one-way valve 61. Once the manual pressure is again removed from disc 20, valve 61 will immediately and automatically close to prevent the entry of contaminants into bowl 11. This entire operational cycle may be repeated as often as required.

Because this drainage device is intended to be used by only one patient and thereafter discarded, it will be appreciated that all materials utilized in the construction of the drainage device are preferably relatively inexpensive components, such as plastic.

It will be apparent from the foregoing description, that the present invention provides a unique valving system for use with a closed wound drainage device. This system provides the advantages of eliminating any possibility that fluids may be forced back into the wound of the patient and that any external contaminants may enter the system. The drainage device may be repeatedly actuated to empty fluids that have been collected therein without disconnecting any tubing which is connected thereto. Thus, in addition to the ease of operation and the obvious safety considerations for the patient, it will also be apparent that the operator of the device is equally as well protected in that handling of the tubing, etc., is greatly simplified.

What is claimed is:

1. A wound drainage device, comprising: a container for both withdrawing and collecting body fluids from a patient; means for increasing and decreasing the internal volume of said container; a fluid inlet port in the wall of said container; first valve means for opening and closing said inlet port; a fluid outlet port in the wall of said container adjacent said fluid inlet port; one-way valve means associated with said outlet port for permitting the emptying of said fluids from said container when said internal volume is decreased but for preventing the entry of contaminants into said container; and gate means movable between a first position and a second position for actuating said first valve means, said gate means when in said first position being effective to open said first valve means and to cover said outlet port, and said gate means when in said second position being effective to close said first valve means and to uncover said outlet port.

2. The wound drainage device of claim 1, wherein said first valve means is a rotary valve and said gate means is connected thereto so that movement of said gate means between its first position and its second position causes said rotary valve to rotate from an open position to a closed position.

3. The wound drainage device of claim 2, wherein said gate means is a generally rectangular housing having an open side adapted to enclose said fluid outlet port when said gate means is in its first position.

4. The wound drainage device of claim 2, wherein said one-way valve means is a duck-bill valve secured within said fluid outlet port.

5. The wound drainage device of claim 1, wherein said container comprises a rigid bowl having a side wall, a bottom wall and an opening defined by the top edge of said side wall; an elastomeric membrane sealed across said edge; and an actuator disc secured to the outer surface of said membrane, said fluid inlet port and said fluid outlet port extending through said side wall.

6. The wound drainage device of claim 1, further comprising, a length of flexible tubing connected at one end to said first valve means and having a connector at its other end for attachment to a wound drainage tube.

* * * * *